(12) United States Patent
Vidovic et al.

(10) Patent No.: US 6,416,958 B2
(45) Date of Patent: Jul. 9, 2002

(54) SELECTIVE APOPTOSIS OF NEOPLASTIC CELLS BY AN HLA-DR SPECIFIC MONOCLONAL ANTIBODY

(75) Inventors: Damir Vidovic, Bellevue, WA (US); Reiner Laus, San Carlos, CA (US)

(73) Assignee: Dendreon Corporation, Seattle, WA (US)

(*) Notice: Subject to any disclaimer, the term of this patent is extended or adjusted under 35 U.S.C. 154(b) by 0 days.

(21) Appl. No.: 09/929,209

(22) Filed: Aug. 13, 2001

Related U.S. Application Data (62) Division of application No. 09/383,663, filed on Aug. 26, 1999.
(60) Provisional application No. 60/098,292, filed on Aug. 28, 1998.

(51) Int. Cl.⁷ .............................. G01N 33/53; C12Q 1/00
(52) U.S. Cl. .............................. 435/7.1; 435/4; 435/7.23
(58) Field of Search .............................. 435/7.1, 4, 7.23

(56) References Cited

FOREIGN PATENT DOCUMENTS

| WO | WO 96/17874 | 6/1996 |
| WO | 00/12560 | * 3/2000 |

OTHER PUBLICATIONS

Chatterjee, et al., *Cancer Immunol.* Immunother. 38: 75–82 (1994).

Gura, et al., *Science* 278: 1041–1042 (1997).

Mendelsohn, J., *Clin. Canc. Res.* 3: 2703–2707, (1997).

Newell, M.K., et al., "Ligation of major histocompayibility complex class II molecules mediates apoptocic cell death in resting B lymphocytes"Proc. Natl. Acad. Sci. USA 90: 10459–10463 (1993).

Schlom, J., *Molecular Goundations of Oncology* pp. 98 (1991).

Truman, J–P., et al., "Lymphocyte programmed cell death is mediated via HLA class II DR" *International Immunology* 6 (6) :887–896 (1994).

Vidovic, D., et al., "Down–regulation of class II major histocompatiblity complex molecules on antigen–presenting cells by antibody fragments" *Eur. J. Immunol.* 25:3349–3355 (1995).

Vidoviÿ, D., and Toral, J.I., "Selective apoptosis of neoplastic cells by the HLA–DR–specific monoclonal antibody" *Cancer Letters* 128 (2):127–135 (1988).

* cited by examiner

Primary Examiner—Louise N. Leary
(74) Attorney, Agent, or Firm—Perkins Coie LLP (57) ABSTRACT

Anti-human major histocompatibility complex (MHC) class II, HLA-DR-specific monoclonal antibodies which can induce apoptosis of HLA-DR positive cells are disclosed. The antibodies are used to specifically eliminate HLA-DR antigen positive tumor cells by cross-linking of HLA-DR. Also disclosed are methods for treating cancer using such antibodies, and compositions containing them.

5 Claims, 5 Drawing Sheets

SELECTIVE APOPTOSIS OF NEOPLASTIC CELLS BY AN HLA-DR SPECIFIC MONOCLONAL ANTIBODY

This application is a division of U.S. application Ser. No. 09/383,663 filed Aug. 26, 1999, which claims the benefit of U.S. Provisional Application No. 60/098,292 filed Aug. 28, 1998, both of which are incorporated herein by reference in their entirety.

FIELD OF THE INVENTION

The present invention relates to monoclonal antibodies (mAb) that specifically react with the HLA-DR antigen and induce apoptosis in HLA-DR expressing cells. In particular, the invention relates to the use of such monoclonal antibodies in the treatment of cancers involving HLA-DR positive cells, and to pharmaceutical compositions containing anti-HLA-DR antibodies.

REFERENCES

Babbitt, et al., *Nature* 317:359–361 (1985).
Borner, et al., *J. Immunol.* 147(1):86–95 (1991).
Bradley, L. M., SELECTED METHODS IN CELLULAR IMMUNOLOGY 153–174, Mishell and Shiigi, Eds., W. H. Freeman & Co., New York (1980).
Brodeur, et al., MONOCLONAL ANTIBODY PRODUCTION TECHNIQUES AND APPLICATIONS, Marcel Dekker, Inc., New York, pp. 51–63 (1987).
Cohen and Duke, *Annu. Rev. Immunol.* 10:267–293 (1992).
Cole, et al., MONOCLONAL ANTIBODIES AND CANCER THERAPY, Alan R. Liss, p. 77 (1985).
David, et al., *Biochemistry* 13:1014 (1974).
Fu and Karr, *Human Immunol.* 39:253–260 (1994).
Goding, MONOCLONAL ANTIBODIES: PRINCIPLES AND PRACTICE, Academic Press, 59–103 (1986).
Harlow and Lane, ANTIBODIES: A LABORATORY MANUAL, Cold Spring Harbor Laboratory, Cold Spring Harbor, N.Y. (1988).
Holland, et al., *Cancer Med.* 2:2697–2828 (1996).
Hoogenboom and Winter, *J. Mol. Biol.* 227:381 (1991).
Hunter, et al., *Nature* 144:945 (1962).
Jones, et al., *Nature* 321:522–525 (1986).
Kohler and Milstein, *Nature* 256:495 (1975).
Kozbor, *J. Immunol.* 133:3001 (1984).
Lampson and Levy, *J. Immunol.* 125:293–299 (1980).
Marks, et al., *J. Mol. Biol.* 222:581 (1991).
Mollick, et al., *J. Immunol.* 146:463–468 (1991).
Munson and Pollard, *Anal. Biochem.* 107:220 (1980).
Newell, et al., *Proc. Natl. Acad. Sci.*, 90(22):10459–10463 (1993).
Nygren, *J. Histochem. and Cytochem.* 30:407 (1982).
Otten and Yokoyama, CURRENT PROTOCOLS IN IMMUNOLOGY, 5.4.1–5.4.19, Ed., Greene & Wiley, N.Y. (1997).
Pain, et al., *J. Immunol. Meth.* 40:219 (1981).
Presta, *Curr. Op. Struct. Biol.* 2:593–596 (1992).
Riechmann, et al., *Nature* 332:323–329 (1988).
Ritts, et al., *Int. J. Cancer* 31:133–141 (1983).
Stocker, et al., *Research Disclosure* 217:155–157 (1982).
Swat, et al., *J. Immunol. Methods* 137:79–87 (1991).
Truman, el al., *Blood* 89(6):1996–2007 (1997).
Truman, el al., *Int. Immunol.* 6(6):887–896 (1994).
Verhoeyen, et al., *Science* 239:1534–1536 (1988).
Vermes, et al., *J. Immunol. Meth.* 184:39–51 (1995).
Vidovic, et al., *Eur. J. Immunol.* 25:3349–3355 (1995).
Vidovic and Toral, *Cancer Lett.* 128:127–135 (1998).
Vitale, et al., *Histochemistry* 100:223–229 (1993).
Wyllie, et al., *J. Pathol.* 142:67–77 (1984).
Zola, MONOCLONAL ANTIBODIES: A MANUAL OF TECHNIQUES, CRC Press, Inc. pp. 147–158 (1987).

BACKGROUND OF THE INVENTION

Class II major histocompatibility complex (MHC) molecules, constitutively expressed on normal antigen presenting cells (APC), are responsible for the presentation of antigen-derived peptides to CD4+ helper T (Th) cells. (Babbitt, et al., 1985; Truman, et al., 1997). Signaling via these molecules initiates the generation of second messengers leading to programmed cell death (PCD or apoptosis) of activated B lymphocytes. Besides antigen presentation, class II molecules transduce signals that can modulate cell growth and certain class II MHC-specific mAb have been shown to induce apoptosis of cancer cells (Newell, et al., 1993). The practical utility of this observation in cancer therapy has been hampered by the intrinsic lack of selectivity, in that the class II MHC-specific antibodies that have been shown to induce apoptosis of cancer cells, also interfere with normal Th cell functions. (Vidovic, et al., 1995). More specifically, the presently available apoptosis-inducing class II-specific mAb recognize epitopes located on the first protein domains of the HLA-DR heterodimer, in apparent close proximity to the peptide-binding site, and these mAbs interfere with antigen presentation, causing a potent in vitro and in vivo inhibition of Th responses (Vidovic, et al., 1995).

Hence, the main problem in using the currently available anti-HLA-DR antibodies for the treatment of cancers involving HLA-DR positive cells is the potential for side effects such as immunosuppression of HLA-DR mediated immune responses based on the lack of definitive specificity of the antibodies for the apoptogenic epitope, and as a result such anti-HLA-DR antibodies may not find practical utility in therapeutic applications.

One approach to overcoming these problems is to administer an anti-Class II (anti-HLA-DR) antibody specifically reactive with tumor cells which can trigger apoptosis in such cells and which does not have immunosuppressive properties associated with the binding to HLA-DR-expressing cells.

SUMMARY OF THE INVENTION

Accordingly, it is an object of the invention to provide a composition for in vivo administration, comprising a monoclonal antibody which specifically binds to HLA-DR-expressing tumor cells and triggers apoptosis of the tumor cells to which it binds.

The present invention is based, in part, on the discovery that antibodies which specifically react with human major histocompatibility complex (MHC) class II can induce apoptosis of cells expressing HLA-DR molecules on their surface.

The antibodies of the present invention are highly specific in that the monoclonal antibodies affect neither the viability nor function of non-neoplastic HLA-DR positive cells.

In one aspect, the invention includes Fab fragments of monoclonal antibodies specific for HLA-DR anchored to a solid support.

The apoptosis-inducing effect of such monoclonal antibodies is associated with a cross-linking of HLA-DR, and monovalent Fab fragments cannot mediate cytotoxicity (Vidovic and Toral, 1998).

According to an important feature of the present invention, the tumoricidal effects of anti-class II MHC mAb can be achieved without simultaneous suppression of class II-dependent immune responses, although both properties are associated with the mAb recognizing an epitope in the first protein domains of HLA-DR.

As outlined herein, the anti HLA-DR antibodies of the present invention specifically bind to the first domains of HLA-DR molecules which are expressed by a variety of types of cancer cells, including, but not limited to B cell cancers. As further outlined herein, the anti-HLA-DR antibodies exert a triggering effect on apoptosis which is specific to HLA-DR positive tumor cells.

An important practical implication of this work is that a mAb, designated Danton; and produced by a hybridoma cell line, also designated Danton; may be effective for the selective antibody-based therapy of HLA class II positive neoplasms, including, but not limited to, blood cell neoplasms, e.g. plasmacytoma/multiple myeloma, Hodgkin's and non-Hodgkin's lymphomas and B cell leukemias. In vitro studies indicate that the Danton mAb does not interfere with normal Th function, therefore, therapy with the Danton mAb should not affect the subject's normal HLA-DR-expressing cells. Accordingly, it would be reasonable to expect fewer side effects than with the currently available therapeutic agents.

These and other objects and features of the invention will become more fully apparent when the following detailed description of the invention is read in conjunction with the accompanying drawings.

BRIEF DESCRIPTION OF THE DRAWINGS

FIGS. 2A and B reflect an analysis of the EBV-LCL cell line, RPMI 1788; FIGS. 2C and D reflect an analysis of the plasmacytoma cell line, MC/CAR; and FIGS. 2E and F reflect an analysis of PBMC (peripheral blood mononuclear cells); with live cells located in the lower right quadrants of the two-dimensional dot-plots.

DETAILED DESCRIPTION OF THE INVENTION

Definitions

The term "antibody" is used in the broadest sense and specifically covers single anti-HLA-DR polypeptide monoclonal antibodies and anti-HLA-DR antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to anti-HLA-DR antibodies which retain the biologic and/or immunologic activities of the Danton anti-HLA-DR antibody described herein.

The term "epitope" as used herein refers to the specific portion of an antigen which interacts with the complementarity determining region (CDR) of an antibody.

The term "Fab fragment" as used herein refers to a partial antibody molecule containing a single antigen binding region which consists of a portion of both the heavy and light chains of the molecule.

The term "F(ab')$_2$ fragment" as used herein refers to a partial antibody molecule containing both antigen binding regions, and which consists of the light chains and a portion of the heavy chains of the molecule.

The term "Fv fragment" as used herein refers to the portion of the antibody molecule involved in antigen recognition and binding.

The term "complementary determining region" (CDR) as used herein refers to the hypervariable region of an antibody molecule which forms a surface complementary to the 3-dimensional surface of a bound antigen.

The term "HLA-DR" as used herein refers to the "human leukocyte antigen" (HLA) DR gene loci and their protein products, the latter being alloantigens expressed on human leukocytes. Alloantigens are the product of polymorphic genes which distinguish self from foreign tissues.

The term "Class II major histocompatibility complex" or "Class II MHC" or "Class II" antigens as used herein refers to antigens that are expressed at various levels on different types of cells and which play an essential role in the recognition of all protein antigens by T cells. Class II MHC molecules typically bind peptides of from 7 to 30 or more amino acids and form complexes that are recognized by antigen-specific CD4+ T cells. The CD4 molecule binds to the second domains of class II molecules.

"Apoptotic cell death" or "programmed cell death" or "apoptosis" as used herein refers to any cell death that results from the complex cascade of cellular events that occur at specific stages of cellular differentiation and in response to specific stimuli. Apoptotic cell death is characterized by condensation of the cytoplasm and nucleus of dying cells.

The term "solid support" as used herein refers to e.g., microtiter plates, membranes and beads, etc. For example, such solid supports may be made of glass, plastic (e.g., polystyrene), polysaccharides, nylon, nitrocellulose, or teflon, etc. The surface of such supports may be solid or porous and of any convenient shape.

The term "tumor" or "cancer" or "neoplasm" as used herein refers to a malignant growth that arises from normal tissue, but grows abnormally with an absence of structure. Tumor or cancer cells generally have lost contact inhibition and may be invasive and/or have the ability to metastasize.

The term "cytotoxic drug" as used herein refers to a drug which is used to inhibit the growth, or facilitate the death of cancer cells. Examples of cytotoxic drugs include chemotherapeutic agents such as ara-C, bleomycin, cisplatin, cladribine, cyclophosphamide, doxorubicin, etoposide, and 5-fluorouracil (5-FU).

By "therapeutically effective amount" as used herein is meant a dose that reduces or eliminates HLA-DR expressing tumor cells by stimulating apoptosis thereof. The exact dose will depend on the purpose of the treatment, and will be ascertainable by one skilled in the art using known techniques.

A "subject" for the purposes of the present invention includes both humans and other animals, particularly mammals. Thus the methods are applicable to both human therapy and veterinary applications. In the preferred embodiment the subject is a mammal, and in the most preferred embodiment the subject is human.

As used herein, the term "improved therapeutic outcome" or "decrease in the number of tumor cells" means a 50% decrease, preferably an 80% decrease, more preferably a 90% decrease, and even more preferably a 100% decrease in either the tumor size, or in the number of detectable circulating cancer cells in the blood and/or affected tissue or organ as determined by examination of a patient and/or samples taken from a patient prior to and following treatment.

The terms "treating", "treatment" and "therapy" as used herein refer to curative therapy prophylactic therapy, and preventative therapy.

Class II MHC and Apoptosis

HLA class II molecules are constitutively expressed on human B lymphocytes and are induced on human T lymphocytes after activation, through which signal transduction via HLA class II has been extensively described. Up to 60% cell death has been observed after stimulation of lymphocytes via HLA-DR molecules. Certain HLA-DR-specific mAbs cause up to a 90% decrease in the cell surface expression of class II molecules, which is also class II isotype-specific, i.e. HLA-DR-specific mAb do not affect the expression of HLA-DP and HLA-DQ molecules. (Truman, et al., 1994).

Previously described anti-HLA-DR mAbs which down-regulate class II expression have been shown to recognize the first (peptide binding) domains of class II heterodimers, and as a result strongly inhibit the activation of class II-restricted human T cells in vitro, in addition to being cytotoxic for B lymphoblastoid cell lines and for a small proportion of normal activated B cells. Their F(ab')$_2$ fragments mediate both down-regulation and cytotoxicity, whereas their monovalent Fab fragments are not cytotoxic, but retain the down-regulatory and T cell inhibitory properties.

Class II molecules transduce signals that can modulate cell growth and class II MHC-specific specific mAb can induce apoptosis of cancer cells (Newell, et al., 1993). Monoclonal antibodies to the first domains of the class II MHC molecule, HLA-DR, prepared as described below serve as the basis for the present invention.

A human major histocompatibility complex (MHC) class II molecule-specific mAb, designated Danton was generated and found to induce apoptosis in tumor cells which express HLA-DR on their surface. The anti-cancer activity of Danton is highly selective in that it affects neither viability nor function of non-malignant HLA-DR positive cells.

Class II MHC

Anti-HLA-DR mAb that are both "immunosuppressive and cytotoxic" may inhibit antigen presentation by recognizing the first domains and binding to an epitope located close to the peptide-binding groove of HLA-DR. The anti-HLA-DR mAb of the present invention, e.g. Danton are "cytotoxic only". Accordingly, it is likely that the precise sequence of HLA-DR to which such a "cytotoxic only" antibody binds, differs from that of antibodies which are both "immunosuppressive and cytotoxic" (Vidovic, et al., 1995).

Apoptotic Cell Death

As described above, apoptosis (programmed cell death) has been associated with the binding of anti-MHC Class II antibodies to Class II-expressing cells. Class II MHC-encoded molecules expressed on the surface of APC (such as B lymphocytes, macrophages, monocytes, dendritic cells, etc.) function as restriction elements for the presentation of antigen to T lymphocytes, an interaction that ultimately leads to activation and differentiation of both cell types.

HLA-DR mediated cell death has been demonstrated to be very rapid, independent of Fc receptors and complement, and non-necrotic. (Truman, et al., 1994; Truman, et al., 1997).

The present discovery relates to the role of anti-HLA-DR antibodies in triggering apoptosis of tumor cells and thus provides methods for inducing programmed cell death in such cells. In a preferred embodiment, the anti-HLA antibodies, and fragments thereof which are capable of cross-linking the HLA-DR antigen, are useful in the study or treatment of conditions which are mediated by tumor cells which express HLA-DR, i.e. to treat or prevent disorders associated with HLA-DR-expressing tumor cells. Accordingly, the antibodies of the present invention are useful to treat various diseases, including, but not limited to, any disease characterized by cancer of B cell origin (where increased apoptosis would be desirable), e.g., Hodgkin's and non-Hodgkin's lymphomas, chronic lymphocytic leukemia, myeloma and plasmacytoma. (Holland, et al., 1996).

Evaluation of the Mechanism of Cell Death

This section describes in vitro assays which are useful for evaluating the extent of apoptotic cell death. Cell death may be detected by staining of cells with propidium iodide (PI), or by use of assays specific to apoptotic cell death, e.g. staining with annexin V (Vermes, et al., 1995). Necrotic cell death may be distinguished from apoptotic cell death by evaluating the results of a combination of the assays for cell viability, as described below, together with microscopic observation of the morphology of the relevant cells.

Assay for Necrotic Cell Death

Necrosis is a passive process in which collapse of internal homeostasis leads to cellular dissolution involving a loss of integrity of the plasma membrane and subsequent swelling, followed by lysis of the cell (Schwartz, el al., 1993). Necrotic cell death is characterized by loss of cell membrane integrity and permeability to dyes such as propidium iodide (PI) which is known by those in the art to bind to the DNA of cells undergoing primary and secondary necrosis (Vitale, et al., 1993; Swat, et al., 1991). Necrosis may be distinguished from apoptosis in that cell membranes remain intact in the early stages of apoptosis. As a consequence dye exclusion assays using PI may be used in parallel with an assay for apoptosis, as described below in order to distinguish apoptotic from necrotic cell death. Fluorescent-activated cell sorter (FACS) based flow cytometry assays using PI allow for rapid evaluation and quantitation of the percentage of necrotic cells.

Assay for Apoptotic Cell Death

Detection of programmed cell death or apoptosis may be accomplished as will be appreciated by those in the art, e.g. by staining with annexin V (Vermes, et al., 1995). The percentage of cells undergoing apoptosis may be measured at various times after stimulation of apoptosis with or without administration of anti-HLA-DR antibodies. The morphology of cells undergoing apoptotic cell death is generally characterized by a shrinking of the cell cytoplasm and nucleus and condensation and fragmentation of the chromatin. (Wyllie, et al., 1984).

Partial DNA degradation in apoptotic B cells has been previously reported (Truman, et al., 1994; Cohen and Duke, 1992). Consistent with this observation, DNA fragmentation was not detected after incubating tumor B cells with an earlier described apoptogenic anti-HLA-DR mAb (Vidovic and Toral, 1988), however, the relative cell size and PI-uptake flow cytometry profiles of these cultures are essentially the same as those previously demonstrated for cells undergoing apoptosis (Newell, et al., 1993; Truman, et al., 1994).

Anti-HLA-DR Antibodies

The present invention provides anti-HLA-DR antibodies. Exemplary antibodies include polyclonal, monoclonal, and humanized antibodies, as well as fragments thereof. The anti-HLA-DR antibodies of the present invention specifically react with a determinant or epitope in the first domains of the HLA-DR protein. In most instances, antibodies made to an epitope or fragment of the HLA-DR protein will be able to bind to the full length protein. Preferably, the antibodies are generated to epitopes unique to the HLA-DR protein; that is, the antibodies show little or no cross-reactivity to other proteins. In a preferred embodiment, the antibodies are generated to the first domains of the HLA-DR molecule The first domains of the HLA-DR correspond to amino acids 1 to 88 and 1 to 96 of the alpha and beta HLA-DR chain, respectively.

The anti-HLA-DR antibodies of the invention specifically bind to HLA-DR proteins. By "specifically bind" herein is meant that the antibodies bind to the protein with a binding constant in the range of at least $10^6$–$10^8$ M, with a preferred range being $10^7$–$10^9$ M.

Polyclonal Antibodies

The anti-HLA-DR antibodies of the present invention may be polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intraperitoneal (IP) injections. The immunizing agent may include the HLA-DR antigen or a fragment or fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The specific immunization protocol may be selected from the numerous protocols which are available, without undue experimentation.

Monoclonal Antibodies

Preferably, the anti-HLA-DR antibodies are monoclonal antibodies. Monoclonal antibodies may be prepared using hybridoma methods, such as those described by Kohler and Milstein, (1975). In a hybridoma method, a mouse, hamster, or other appropriate host animal, is injected with an immunizing agent to elicit lymphocytes that produce or are capable of producing antibodies that will specifically bind to the immunizing agent. Alternatively, the lymphocytes may be immunized in vitro.

The immunizing agent includes the HLA-DR polypeptide, fragments or a fusion protein thereof. Generally, either PMBC are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, 1986). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection (ATCC), Rockville, Md. Human myeloma and mouse-human heteromyeloma cell lines also have been described for the production of human monoclonal antibodies (Kozbor, 1984; Brodeur, et al., 1987).

The culture medium in which the hybridoma cells are cultured can then be assayed for the presence of monoclonal antibodies directed against the HLA-DR polypeptide. The binding specificity of monoclonal antibodies produced by the hybridoma cells may be determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, (1980).

After the desired hybridoma cells are identified, the clones may be subcloned by limiting dilution procedures and grown by standard methods [Goding, supra]. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Digestion of antibodies to produce fragments thereof, particularly, F(ab), F(ab')$_2$ and Fv fragments, can be accomplished using routine techniques known in the art.

The methods of the present invention require that anti-HLA-DR antibodies be bivalent, in order to facilitate cross-linking of HLA-DR molecules and thereby stimulate apoptosis. Accordingly one or more fragments of anti-HLA-DR antibodies may be bound to a solid support thereby facilitating the cross-linking of HLA-DR.

Humanized Antibodies

The anti-HLA-DR antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding regions of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al., 1986; Riechmann, et al., 1988; and Presta, 1992).

Methods for humanizing non-human antibodies are well known in the art. Generally, a humanized antibody has one or more amino acid residues introduced into it from a source which is non-human. Humanization can be essentially performed following the method of Winter and co-workers (Jones, et al., 1986; Riechmann, et al., 1988; Verhoeyen, et al., 1988), by substituting rodent CDRs or CDR sequences for the corresponding sequences of a human antibody. Accordingly, such "humanized" antibodies are chimeric antibodies wherein substantially less than an intact human variable domains has been substituted by the corresponding sequence from a non-human species. In practice, humanized antibodies are typically human antibodies in which some CDR residues and possibly some framework residues are substituted by residues from analogous sites in rodent antibodies.

Human antibodies can also be produced using various techniques known in the art, including phage display libraries (Hoogenboom and Winter, 1991; Marks, et al., 1991). Exemplary additional techniques that are available for the preparation of human monoclonal antibodies are described in Cole et al., (1985) and Boemer, et al., (1991).

Uses for Anti-HLA-DR Antibodies

The anti-HLA-DR antibodies of the present invention have various utilities. For example, anti-HLA-DR antibodies may be used in diagnostic assays for, and therapy involving, HLA-DR expressing tumor cells, e.g., detecting expression of such cells in tissues or serum, and serving as the basis for therapy to improve the clinical outcome of subjects with such tumors, respectively.

Various diagnostic assay techniques known in the art may be used, such as competitive binding assays, direct or indirect sandwich assays and immunoprecipitation assays conducted in either heterogeneous or homogeneous phases (Zola, 1987). The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Molecules which facilitate specific binding also include pairs, such as biotin and streptavidin, digoxin and antidigoxin, etc. One of the members of a pair of such molecules which facilitate specific binding may be labeled such that it provides for detection in accordance with known procedures, wherein the label can directly or indirectly provide a detectable signal. Any method known in the art for conjugating the antibody to the detectable moiety may be employed, including those methods described by Hunter, et al., (1962); David, et al., (1974); Pain, et al., (1981); and Nygren, (1982).

Therapy with anti-HLA-DR antibodies is further described below.

Anti-HLA-DR antibodies also are useful for the affinity purification of HLA-DR expressing cancer cells from cell culture or natural sources. In this process, the antibodies against a HLA-DR are immobilized on a suitable support, such a Sephadex resin or filter paper, using methods well known in the art. The immobilized antibody is then contacted with a sample containing HLA-DR expressing cancer cells to be purified, and thereafter the support is washed with a suitable medium that will remove substantially all the material in the sample except the HLA-DR expressing cancer cells, which are bound to the immobilized antibody. Finally, the support is washed with another suitable medium that will release the HLA-DR expressing cancer cells from the antibody.

Biological Effects of Anti-HLA-DR Specific Monoclonal Antibodies

Class II MHC specific mAbs are described which recognize the first domains of HLA-DR. The antibody or CDR region of the HLA-DR specific mAbs of the invention is immunoreactive with, and capable of inducing apoptosis in, tumor cells that express detectable levels of the HLA-DR. The HLA-DR-specific mAb, Danton, has demonstrated in vitro specificity for induction of apoptosis in tumor (plasmacytoma MC/CAR) cells relative to nonneoplastic cells both of which express HLA-DR. (Example 2 and FIGS. 2A–4B).

Figure 5:
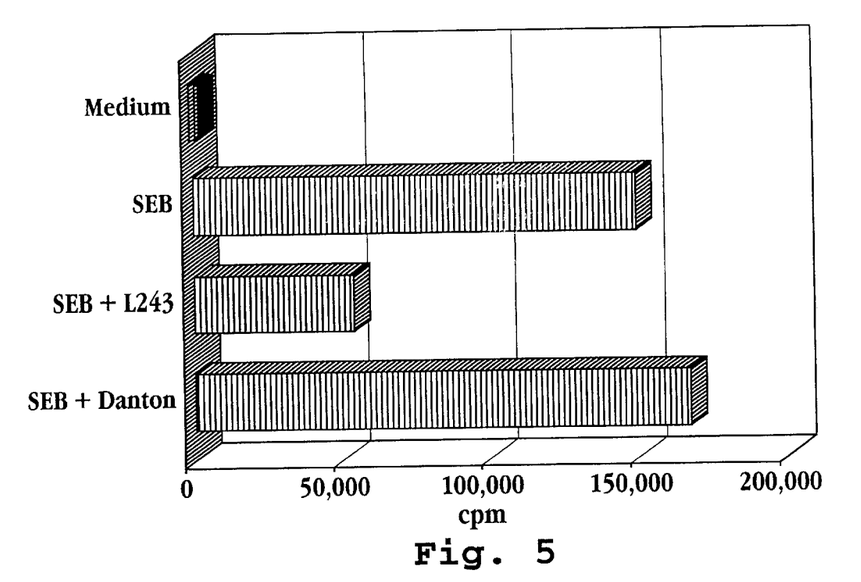
FIG. 5 shows the absence of immunosuppressive effects of the Danton mAb relative to a medium control, staphylococcal enterotoxin B (SEB) alone and SEB plus a different anti-HLA-DR mAb, L243, on the SEB specific in vitro proliferative response of human PBMC, as indicated by [$^3$H]thymidine incorporation.

In addition, the lack of interference with normal Th responses by Danton has been demonstrated in vitro. (See Example 2 and FIG. 5).

In Vivo Cancer Therapy with Anti-HLA-DR Antibodies

The antibodies of the present invention are therapeutically effective and can stimulate apoptotic cell death of tumor cells that express the HLA-DR antigen. These findings raise the possibility of a selective antibody-based anti-tumor therapy for HLA-DR positive cancers, particularly those of the blood.

The tumoricidal effects of anti-class II MHC mAb can be achieved without simultaneous suppression of class II-dependent immune responses, although both properties are associated with mAb recognizing the first domains of the protein.

Antibodies having the desired therapeutic effect may be administered in a physiologically acceptable carrier to a host, and may be administered in a variety of ways, e.g., parenterally, subcutaneously (SC), intraperitoneally (IP), intravenously (IV), etc. Depending upon the manner of introduction, the antibodies may be formulated in a variety of ways. The concentration of therapeutically active antibody in the formulation may vary from about 1 mg/ml to 1 g/ml.

Preferably, the antibody is formulated for parenteral administration in a suitable inert carrier, such as a sterile physiological saline solution. For example, the concentration of antibody in the carrier solution is typically between about 1–100 mg/ml. The dose administered will be determined by route of administration. Preferred routes of administration include parenteral or IV administration. A therapeutically effective dose is a dose effective to produce a significant increase in apoptotic cell death of HLA-DR expressing neoplastic cells. A significant increase in apoptotic cell death of HLA-DR expressing neoplastic cells is a 2-fold increase, more preferably a 5-fold increase, even more preferably a 10-fold increase, and most preferably a 20-fold or greater increase in apoptotic cell death of HLA-DR expressing cells relative to cells which do not express a detectable amount of HLA-DR.

According to an important feature of the invention, the anti-HLA-DR antibody may be administered alone, or in combination with other anti-cancer agents, such as chemotherapeutic agents, for example, cisplatin, taxol, methotrexate, etc.; tumor necrosis factor-alpha (TNF-α); FADD, PMA; ionomycin; staurosporine or Rituxan®.

The therapeutically effective amount of an anti-HLA-DR antibody, e.g. Danton, can be estimated by comparison with established effective doses for known antibodies, taken together with data obtained for Danton in in vitro models for the apoptotic cell death of HLA-DR positive tumor cells, as described herein. As is known in the art, adjustments in the dose may be necessary due to antibody degeneration, systemic versus localized delivery, as well as the age, body weight, general health, sex, diet, time of administration, drug interactions and the severity of the condition. Such adjustments may be made and appropriate doses determined by one of skill in the art through routine experimentation.

The following examples serve to more fully describe the manner of using the abovedescribed invention, as well as to set forth the best modes contemplated for carrying out various aspects of the invention. It is understood that these examples in no way serve to limit the true scope of this invention, but rather are presented for illustrative purposes.

All patent and literature references cited in the present specification are hereby incorporated by reference in their entirety.

EXAMPLE 1

Generation of Danton mAb

The mouse monoclonal antibody Danton, was prepared according to standard techniques known in the art (Harlow and Lane, 1988). Inbred laboratory mice of BALB/c strain (Jackson Laboratory, Bar Harbor, Me.), hyperimmunized with an immunogen were donors of immune B cells. BALB/c-derived mutant B lymphoma line M12.C3, transfected with chimeric human/mouse class II gene was used as the immunogen. The MHC class II molecule expressed by this transfectant (designated M12.C3.25) was composed of the first extracellular (alpha1 and beta1) domains of the HLA-DR, and the second extracellular (alpha2 and beta2), transmembrane and intra cytoplasmic domains of the corresponding mouse MHC class II molecule H2-E. (Vidovic, et al., 1995). Mice were immunized at monthly intervals with 5 IP injections, each consisting of $10^7$ (-irradiated (100 Gy) M12.C3.25 cells resuspended in 1 ml of phosphate buffered saline (PBS). Three days after the last injection, immune splenocytes were fused with the HAT-sensitive Ig-negative mouse myeloma cells PAI-0 (Stocker, et al., 1982). The supernatant fluids of single hybridoma cultures were screened for their toxicity on EBV-LCL RPMI 1788 after a 4 hour incubation at 4 EC. A colony, which was identified based on stable secretion of a mAb having the desired bioactivity, was designated "Danton" (DR-specific antibody for oncology), and subcloned two times by the limiting dilution method. Using the standard isotyping kit (Zymed, South San Francisco, Calif.), the mAb Danton was found to be of a mouse IgG16 isotype.

EXAMPLE 2

Evaluation of In Vitro Tumoricidal Effects of the Danton mAb

Human cell lines MC/CAR (plasmacytoma) (Ritts, et al., 1983), and RPMI 1788 (Epstein-Barr virus transformed lymphoblastoid B cell line, EBV-LCL) were purchased from ATCC (Rockville, Md.). Cells were cultured at the density of $10^5$/ml in IMDM medium supplemented with 10% FCS, 2 mM L-glutamine, 0.1 mg/ml kanamycin sulfate and $3\times10^{-5}$ M 2-ME (Gibco, Grand Island, N.Y.) at 37EC in a humidified atmosphere containing 5% $CO_2$ (tissue culture incubator). Sterile filtered supernatant fluids of the HLA-DR-specific mAb-secreting mouse B cell hybridoma cell lines Danton and 10F12, cultured at $5\times10^5$ cells/ml, were added to the human cells at the final concentration of 20%. Following the indicated coculture period, cells were washed and their viability was determined after an additional 5 minute incubation with 1 µg/ml of propidium iodide (PI, Sigma, St. Louis, Mo.) and a subsequent analysis of cell size (forward light scatter, FSC) vs. red PI fluorescence on a FACScan® flow cytometer using CELLQuest 3.1f software (Becton-Dickinson, San Jose, Calif.) (Otten and Yokoyama, 1997, Coligan, et al., 1997)]. Live cells were shown to actively exclude PI, while dead cells took it up in a direct proportion to the accessibility of their DNA (Swat, et al., 1991).

Figure 1:
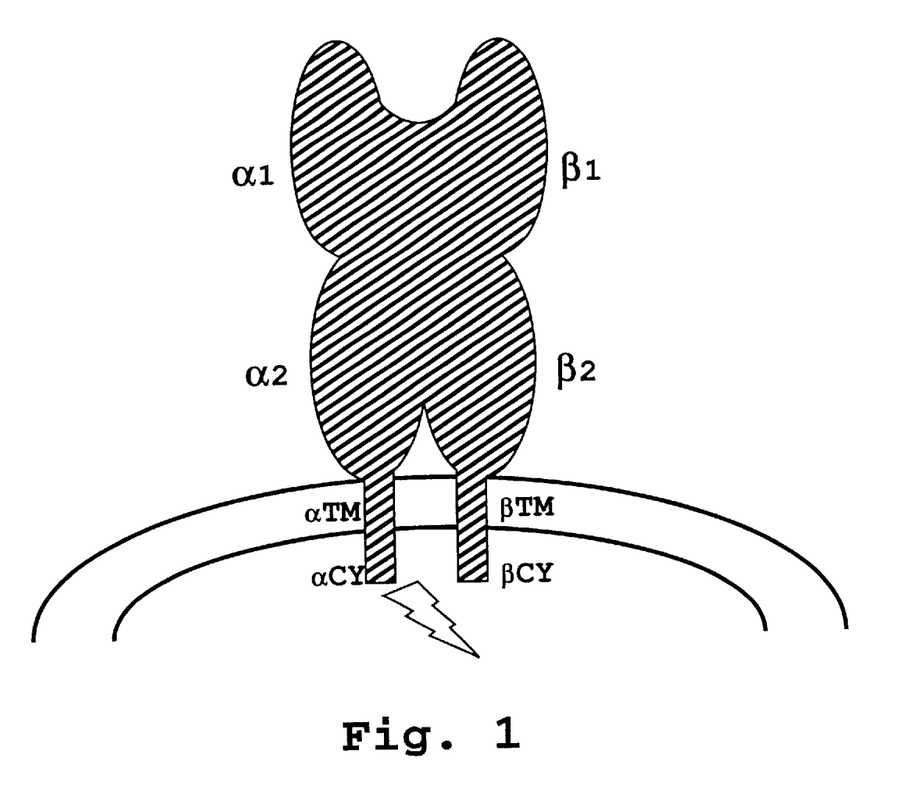
FIG. 1 shows a general epitope map of HLA-DR molecule indicating: CY, cytoplasmic tail; TM, transmembrane part; α1 & β1, the first (extracellular) domains of alpha and beta chains, respectively; and α2 & β2, the second (extracellular) domains of alpha and beta chains, respectively.
Figure 2A:
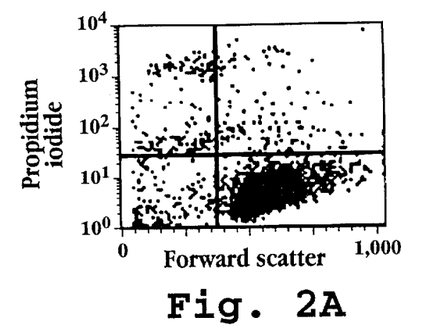
FIGS. 2A–F show the results of FACS analysis indicating the viability of different cell populations after 16 hours coculture in medium alone (first column) or in the presence of the Danton mAb (second column).
Figure 2B:
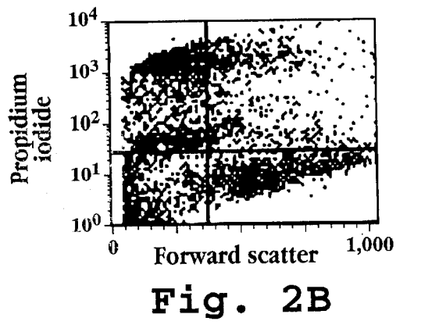
Figure 2C:
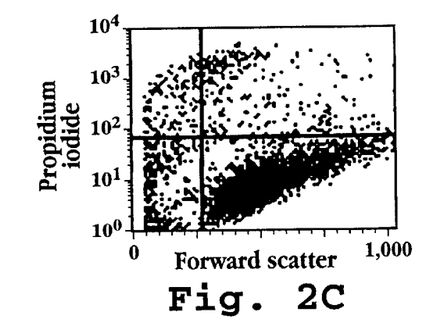
Figure 2D:
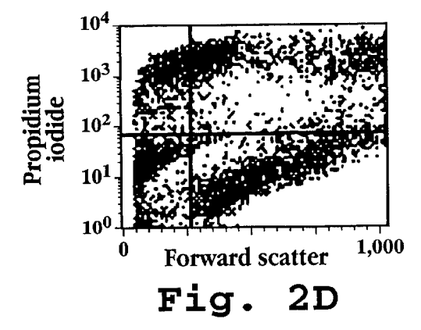
Figure 2E:
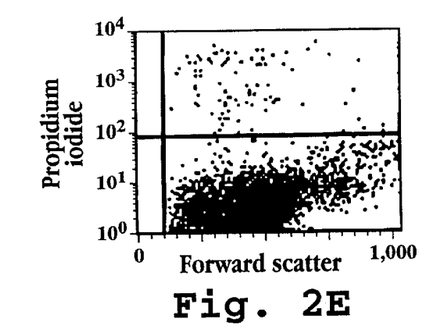
Figure 2F:
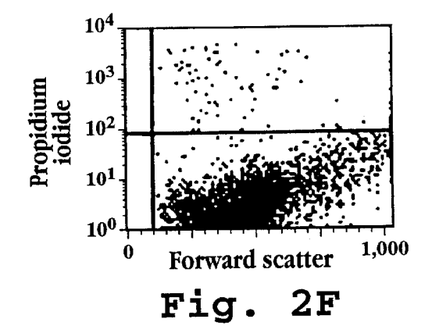
Figure 3A:
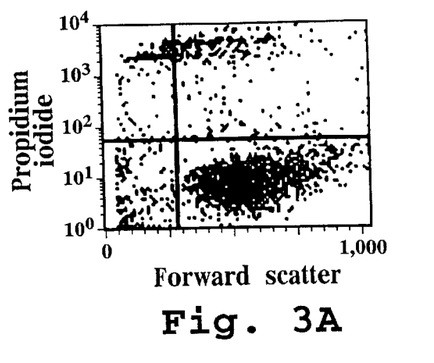
FIGS. 3A–F show the results of FACS analysis indicating the viability of the EBV-LCL cell line, RPMI 1788 (first column) and the plasmacytoma cell line, MC/CAR (second column) after 16 h coculture with in medium alone (FIGS. 3A, D); in the presence of the Danton mAb (FIGS. 3B, E); and in the presence of the 10F12 mAb (FIGS. 3C, F).
Figure 3B:
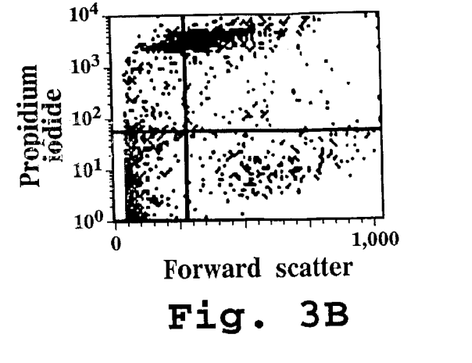
Figure 3C:
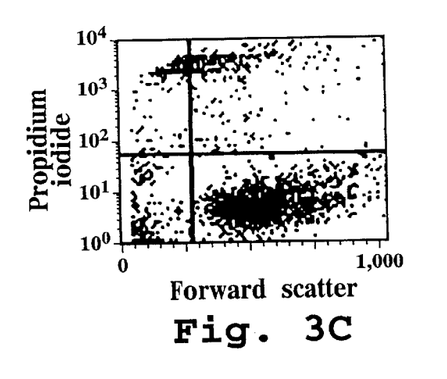
Figure 3D:
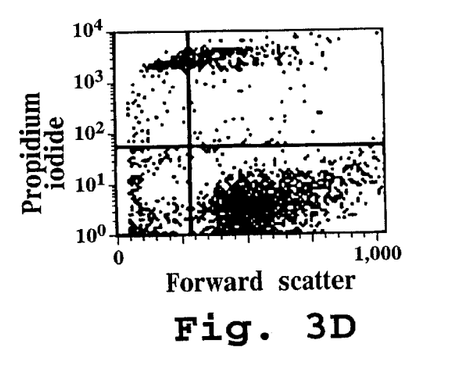
Figure 3E:
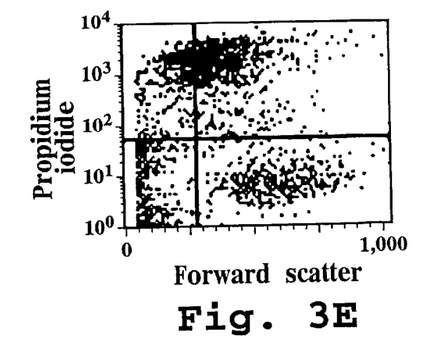
Figure 3F:
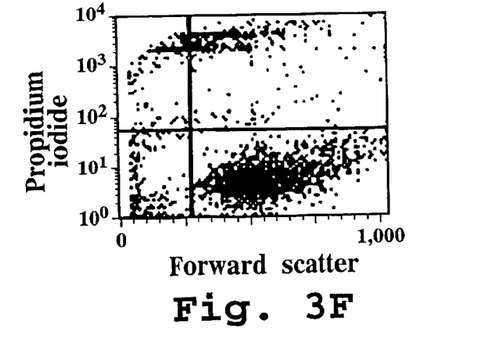

The ability of the Danton mAb to induce apoptosis of neoplastic cells was shown by coculture of 2 independent human B cell tumor lines (EBV-LCL RPMI 1788 and plasmacytoma MC/CAR which resulted in greater than 75% cell death (FIGS. 2A–D). The cytotoxic effect was completely absent in normoplastic (i.e., non-neoplastic) HLA-$DR^+$ lymphocytes obtained from human peripheral blood (FIGS. 2E–F). In contrast to Danton, 10F12, an anti-DR mAb specific for a common epitope located within the second protein domains, did not affect viability of MC/CAR (FIGS. 3A–F).

Figure 4A:
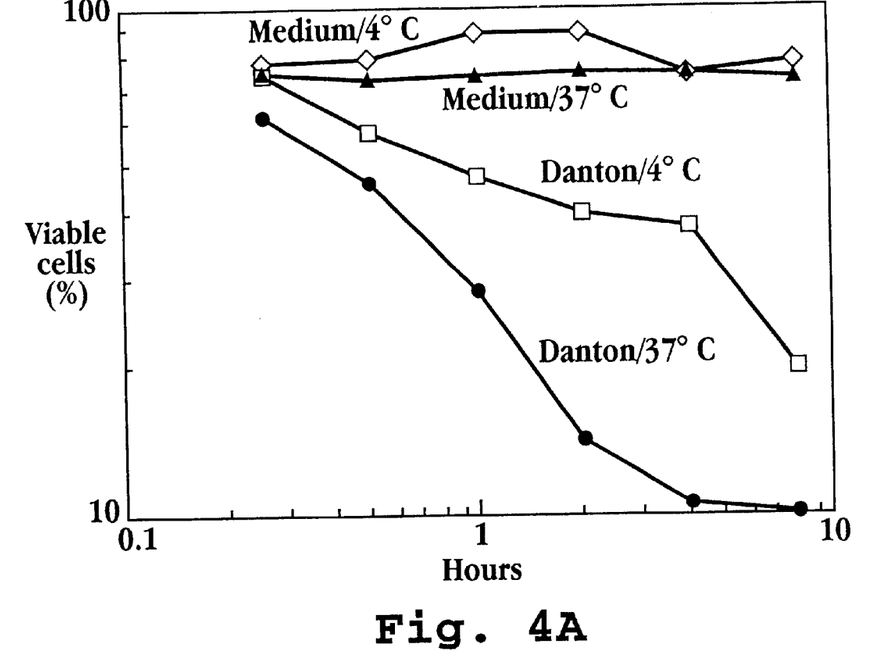
FIGS. 4A and B show the viability of EBV-LCL RPMI 1788 cells after incubation with the Danton mAb under different temperature conditions as indicated, for 0.1 to 10 hours (FIG. 4A) and 1 to 21 days (FIG. 4B).
Figure 4B:
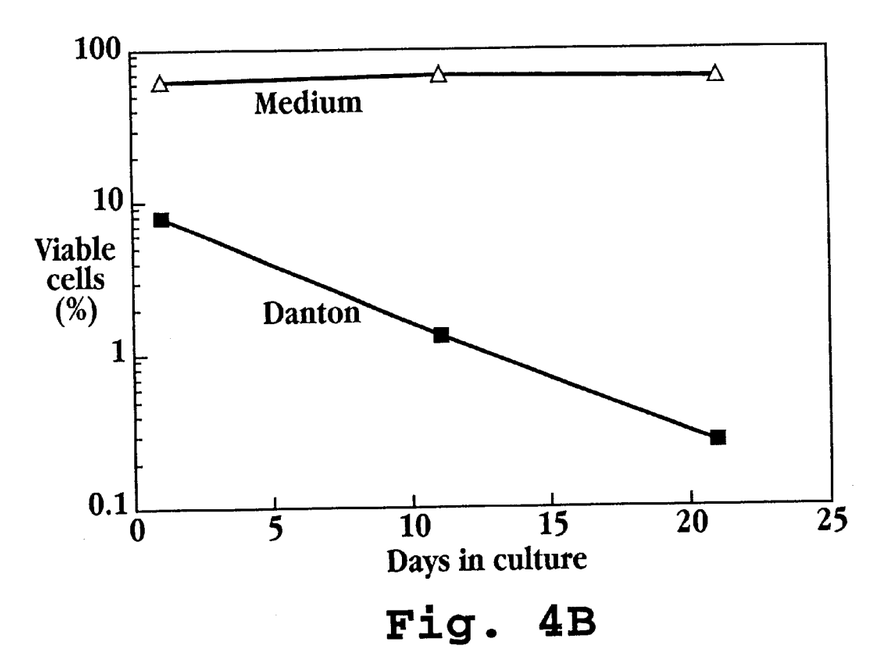

The cytotoxicity time course under two different incubation conditions is shown in FIG. 4A. It appears that Danton-induced cell death is temperature dependent; with the faster rate at human body temperature (37° C., the cytotoxic effect evident within 30 minutes, and retarded, yet still occurring at 4° C. (the cytotoxic effect evident after 1–2 hours). The undiminished tumorotoxicity of Danton even after the prolonged (3 weeks) coculture with tumor cells indicates their inability to become resistant to this mAb (FIG. 4B).

EXAMPLE 3

Evaluation of Immunosuppressive Effects of the Danton mAb

HLA-DR dependent in vitro proliferative responses of human $T_h$ cells against Staphylococcal enterotoxin B (SEB) were generated as previously described (Mollick et al., 1991). Briefly, $2\times10^5$ fresh human PBMC, obtained from a heparinized blood by Ficoll separation, were cultured with 0.1 ug/ml SEB (Toxin Technology, Sarasota, FL) in 0.2 ml of the IMDM medium supplemented with 10% FCS, 2 mM L-glutamine, 0.1 mg/ml kanamycin sulfate and $3\times10^{-5}$ M 2-ME at 37° C. in a humidified atmosphere containing 5% $CO_2$ (tissue culture incubator) for 3 days. Sterile filtered supernatant fluids of the HLA-DR-specific mAb-secreting mouse B cell hybridoma cell lines Danton and L243 (ATCC, Rockville, Md.) (Lampson and Levy, 1980; Fu and Karr, 1994), cultured at $5\times10^5$ cells/ml, were added at the initiation of the assay at the final concentration of 20%. T cell proliferation of triplicate cultures was measured by [$^3$H] thymidine incorporation during the final 16 hours (Bradley, 1980). While mAb L243 suppressed about 70% of SEB-triggered T cell response, Danton had no effect (FIG. 5), although both mAbs recognize epitopes on the first HLA-DR domains.

EXAMPLE 4

Evaluation of In Vivo Anti-tumor Activity of the Danton mAb

Figure 6:
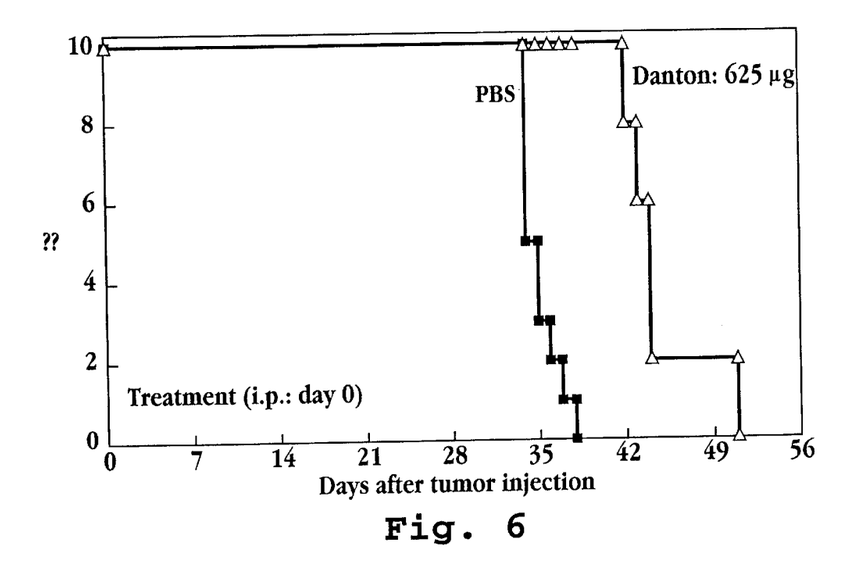
FIG. 6 shows the survival of scid mice injected with the HLA-DR$^+$ human plasmacytoma cell line, MC/CAR; and treated with either mAb Danton (open triangles), or phosphate buffered saline (PBS; filled squares).

The in vivo anti-tumor activity of Danton was evaluated in severe combined immunodeficiency inbred (scid) mice injected with the HLA-DR positive human plasmacytoma MC/CAR. Twenty 8-week-old mice, randomized according to their body weight were injected IP with $10^7$ MC/CAR cells in 0.1 ml RPMI 1640 medium per mouse (Ritts, et al., 1983). Subsequently, half the animals received a single IP dose of 0.625 mg Danton mAb in 0.1 ml of PBS. The remaining mice were given corresponding IP injections of 0.1 ml PBS. Mice were monitored daily, and their survival recorded. As shown in FIG. 6, Danton exhibited a notable therapeutic activity, significantly prolonging the survival of tumor-bearing mice.

Although the invention has been described with respect to particular treatment methods and composition, it will be apparent to those skilled that various changes and modifications can be made without departing from the invention.

It is claimed:

1. A method of triggering apoptosis, comprising administering to a subject, a therapeutically effective amount of an anti-HLA-DR antibody effective to stimulate apoptosis in HLA-DR-expressing tumor cells.

2. The method of claim 1 wherein the therapeutic outcome of the subject is improved following said administration.

3. The method of treating cancer according to claim 2 wherein said cancer involves HLA-DR expressing cells and is selected from the group consisting of plasmacytoma/multiple myeloma, Hodgkin's lymphomas, non-Hodgkin's lymphomas and B cell leukemias.

4. The method of claim 2 wherein the therapeutic anti-HLA-DR antibody is administered intravenously (IV).

5. The method of claim 2 wherein the therapeutic anti-HLA-DR antibody is administered parenterally.

* * * * *